United States Patent
Decoodt et al.

(10) Patent No.: US 8,123,950 B2
(45) Date of Patent: Feb. 28, 2012

(54) PROCESS AND APPARATUS FOR SIMULATED MOVING BED SEPARATION COMPRISING BYPASS LINES IN EVERY OTHER BED AND WITH A MODULATED BYPASS FLUID FLOW RATE

(75) Inventors: Xavier Decoodt, Carrieres S/Seine (FR); Gerard Hotier, Rueil Malmaison (FR); Philibert LeFlaive, Le Domaine de Chanteclair (FR); Damien Leinekugel Le Cocq, Lyons (FR)

(73) Assignee: IFP Energies Nouvelles, Rueil-Malmaison Cedex (FR)

( * ) Notice: Subject to any disclaimer, the term of this patent is extended or adjusted under 35 U.S.C. 154(b) by 167 days.

(21) Appl. No.: 12/757,101

(22) Filed: Apr. 9, 2010

(65) Prior Publication Data
US 2010/0258505 A1 Oct. 14, 2010

(30) Foreign Application Priority Data
Apr. 10, 2009 (FR) .................................. 09 01784

(51) Int. Cl.
*B01D 15/08* (2006.01)
(52) U.S. Cl. ..... 210/659; 210/635; 210/656; 210/198.2; 585/825; 585/828
(58) Field of Classification Search .................. 210/635, 210/656, 659, 662, 198.2; 585/825, 828
See application file for complete search history.

(56) References Cited

U.S. PATENT DOCUMENTS

| | | | |
|---|---|---|---|
| 5,578,215 A | 11/1996 | Hotier et al. | |
| 5,972,224 A * | 10/1999 | Hotier et al. | 210/659 |
| 6,110,364 A * | 8/2000 | Hotier et al. | 210/198.2 |
| 6,284,200 B1 | 9/2001 | Hotier | |
| 6,537,451 B1 * | 3/2003 | Hotier | 210/198.2 |
| 6,797,175 B2 * | 9/2004 | Hotier | 210/659 |

(Continued)

FOREIGN PATENT DOCUMENTS

| | | |
|---|---|---|
| EP | 0 688 589 A1 | 12/1995 |
| EP | 0 846 483 B1 | 5/2003 |
| WO | WO 2007/144476 A1 | 12/2007 |

OTHER PUBLICATIONS

Search Report of FR 0901784 (Nov. 5, 2009).

*Primary Examiner* — Ernest G Therkorn
(74) *Attorney, Agent, or Firm* — Millen, White, Zelano & Branigan, P.C.

(57) ABSTRACT

A process for separating a feed F by simulated moving bed adsorption in a SMB device is described, the device comprising external bypass lines $L_{i/i+1}$ which directly connect two successive plates $P_i$, $P_{i+1}$, the index i being either even or (exclusive of the foregoing) odd, along the whole length of the column, in order to flush said plates, in which each of the bypass lines $L_{i/i+1}$ comprises automated means for regulating the flow rate in the bypass lines, the degree of opening of said regulating means being defined by the following three rules:

a) establishing a flow rate corresponding to an oversynchronicity in the range 15% to 30% in all of the open bypass lines of zone 1;

b) establishing a flow rate corresponding to the synchronicity to within plus or minus 8% in all of the open bypass lines of zones 2 and 3;

c) establishing a flow rate corresponding to an oversynchronicity in the range 20% to 40% in all of the open bypass lines of zone 4.

7 Claims, 2 Drawing Sheets

U.S. PATENT DOCUMENTS

| | | | |
|---|---|---|---|
| 8,049,055 B2 * | 11/2011 | Decoodt et al. | 585/828 |
| 2004/0063992 A1 | 4/2004 | Chiang et al. | |
| 2009/0209736 A1 | 8/2009 | Theoleyre et al. | |
| 2010/0048973 A1 * | 2/2010 | Decoodt et al. | 585/822 |
| 2010/0258505 A1 * | 10/2010 | Decoodt et al. | 210/661 |
| 2011/0201865 A1 * | 8/2011 | Decoodt et al. | 585/822 |

* cited by examiner

PROCESS AND APPARATUS FOR SIMULATED MOVING BED SEPARATION COMPRISING BYPASS LINES IN EVERY OTHER BED AND WITH A MODULATED BYPASS FLUID FLOW RATE

FIELD OF THE INVENTION

The invention relates to the field of separations of chemical, natural or synthetic products which are difficult to separate by distillation. A family of processes and associated devices is used, known as simulated moving bed processes or separation devices, either in simulated counter current or in simulated co-current mode, which will hereinafter be known by the generic term SMB. Thus, in the remainder of the text reference will be made to the SMB process or device or SMB separation or SMB units.

The fields concerned are particularly but not exclusively:
  separation of normal paraffins from branched paraffins, napthenes and aromatics;
  olefin/paraffin separation;
  separation of para-xylene from other aromatic C8 isomers;
  separation of meta-xylene from other aromatic C8 isomers
  separation of ethylbenzene from other aromatic C8 isomers.

Many other applications exist beyond the refinery and petrochemicals complex; those which may be cited include glucose/fructose separation, the separation of positional isomers of cresol, separation of optical isomers, etc.

PRIOR ART

SMB separation is well known in the art. As a general rule, a column operating in simulated moving bed mode comprises at least three operating zones, and optionally four or five operating zones, each of said zones being constituted by a certain number of successive beds, and each zone being defined by its position included between a supply point and a withdrawal point. Typically, a SMB column is supplied by at least one feed F to be fractionated and a desorbent D (sometimes termed the eluent), and at least one raffinate R and an extract E are withdrawn from said column.

The supply and withdrawal points are regularly shifted over time, in the same direction and retaining their relative position, by a value corresponding to one bed. The time interval separating two successive shifts of the supply and withdrawal points is termed the period.

By definition, each of the operational zones is designated by a number:
  zone 1=zone for desorption of compounds in the extract, included between injection of the desorbent D and removal of the extract E;
  zone 2=zone for desorption of compounds in the raffinate, included between the removal of the extract E and the injection of the feed to be fractionated F;
  zone 3=zone for adsorption of the compounds in the extract, included between the injection of the feed and the withdrawal of the raffinate R;
  and preferably a zone 4 located between the withdrawal of the raffinate and the injection of the desorbent.

The prior art describes in detail various devices and processes for carrying out simulated moving bed feed separation.

Patents which may in particular be cited are U.S. Pat. No. 2,985,589, U.S. Pat. No. 3,214,247, U.S. Pat. No. 3,268,605, U.S. Pat. No. 3,592,612, U.S. Pat. No. 4,614,204, U.S. Pat. No. 4,378,292, U.S. Pat. No. 5,200,075, U.S. Pat. No. 5,316,821. Those patents also describe the function of an SMB in detail.

SMB devices typically comprise at least one column (and frequently two) divided into several successive beds of adsorbant $A_i$, said beds being separated by plates $P_i$, each plate $P_i$ comprising one, two or four chambers which can carry out sequential operations of supply of the feed or injection of the desorbent and extraction of the raffinate or extract.

The present invention comes into the category of single-chamber devices, i.e. which can carry out both supply and withdrawal of the various streams using said chamber.

As will be described in more detail below, the plates are generally divided into panels, each panel comprising a chamber for supply and withdrawal of streams.

Each of the plates $P_i$ typically comprises a plurality of distributor-mixer-extractor panels termed "DME plates" supplied via distribution/extraction lines or systems. The plates may be of any type and any geometry.

Said panels correspond to adjacent sectors in the section of the column, for example panels with angular sectors such as those described in U.S. Pat. No. 6,537,451 or panels with parallel sectors such as those described in U.S. Pat. No. 6,797,175.

The present invention is compatible with any type of division of a plate into different panels.

Preferably, the separation column of the invention comprises DME plates of the type with parallel sectors and di-symmetrical supplies.

Distribution over each of the beds requires that the principal stream deriving from the preceding bed be collected, that a supplemental fluid or secondary fluid be capable of being injected while mixing the two fluids as much as possible, or it requires that a portion of the collected fluid should be capable of being removed, of being extracted to send it out of the device and also a fluid should be capable of being re-distributed over the next bed.

A generic problem with all SMB devices is that of minimizing the pollution generated by the liquid found in the various zones of the circuit or circuits for supplying and withdrawing fluids to or from the plates during modifications of the supply and withdrawal points during operation of the SMB.

When during the operational sequence a line, chamber or supply zone for a plate $P_i$ is no longer flushed by a process fluid, it becomes a dead zone in which the liquid stagnates, and it is moved again only when another process fluid moves in it once more. The operation of the SMB means that this is a process fluid which is a different fluid from the fluid stagnating in the line under consideration.

The mixing or the movement over a brief time interval of fluids with substantially different compositions introduces perturbations into the concentration profile of the zone under consideration compared with the ideal operation, for which compositional discontinuities should be avoided.

Another problem resides in possible re-circulation between the various zones of the same plate, and more generally over the whole of the distribution/extraction system of the same plate, due to very small pressure differences between the various zones of the plate, which induces further perturbation compared with ideal operation.

In order to overcome the problems due to re-circulation and dead zones, various solutions are known in the prior art:
  a) a proposal has already been made to flush the distribution/extraction system of a given plate using desorbent or the relatively pure desired product. That technique avoids pollution of the desired product during its extraction. However, since the flushing liquid has a very different composition from the liquid it displaces, this introduces compositional discontinuities which are prejudicial to ideal operation. This first flushing variation typically carried out flushes of short duration with a high concentration gradient. Such flushes are of short duration precisely in order to limit the effects of compositional discontinuities.

b) As described in U.S. Pat. Nos. 5,972,224 and 6,110,364, another solution consists of passing a majority of the principal stream into the interior of the column and a minority of that stream (typically 1% to 20% of the principal stream) outwardly via external bypass lines between successive plates. This flushing of the distribution/extraction system at one plate by a stream deriving from the plate above is typically carried out continuously, so that the lines and zones of the distribution/extraction system are no longer "dead" but are constantly flushed.

Such a system with continuous flushing via bypass lines is disclosed in patent FR-2 772 634. The diameter of the bypass lines is generally small and the lines include a small diameter valve which reduces the cost of the system.

According to the teaching of U.S. Pat. Nos. 5,972,224 and 6,110,364, the distribution/extraction system of a given plate is intended to be flushed with a liquid having a composition very close to that of the displaced liquid (liquid present in the distribution system or moving on a plate). Thus, the mixing of fluids with different compositions is minimized, and compositional discontinuities are reduced.

To this end, U.S. Pat. Nos. 5,972,224 and 6,110,364 recommend using flush flow rates in the bypass lines such that the rate of transit in each bypass line is substantially the same as the rate of advance of the concentration gradient in the principal stream of the SMB. This is thus termed "synchronous" flushing or "synchronous flow rate" flushing. Thus, the various lines and volumes are flushed by a fluid which has a substantially identical composition to that of the liquid therein, and the liquid moving in a bypass line is re-introduced at a point where the composition of the principal stream is substantially identical.

The flushes are thus synchronous and with a low or zero concentration gradient.

According to the teaching of the cited patents, a flush is termed "synchronous" when the flush flow rate $QS_{i/i+1}$ from one plate $P_i$ to the next plate $P_{i+1}$ is equal to V/ST in which V is the cumulative volume of the distribution systems of the plates $P_i$ (i.e. $V_i$) and $P_{i+1}$ (i.e. $V_{i+1}$) and of the volume of the bypass line between said two plates (i.e. $VL_{i/i+1}$), and ST is the switch time of the SMB between two successive switches of the supplies/extractions.

Thus, we have:

Synchronous flow rate=$QS_{i/i+1}=(V_i+V_{i+1}+VL_{i/i+1})$/ST, where:

$QS_{i/i+1}$=flow rate of flush from plate $P_n$ to the next plate (typically lower) $P_{i+1}$;

$V_i$=volume of distribution/extraction system of outflow plate $P_i$;

$V_{i+1}$=volume of distribution/extraction system of inflow plate $P_{i+1}$;

$VL_{i/i+1}$=volume of bypass line between $P_i$ and $P_{i+1}$;

ST=switch time.

Synchronous flushing is typically carried out at a controlled rate, adapted to each of the zones, of 50% to 150% of the synchronous flow rate in said zones, and ideally 100% of the synchronous flow rate. The flow rates in the bypass lines of the 4 zones of the SMB are controlled by regulating means in each bypass line. As an example, the skilled person could use a flow rate of 90% of the synchronous flow rate in all of these zones, or 110%, or even any other value close to 100% of the synchronous flow rate. However, provided that regulating means exist, the skilled person, following the teaching of the patent cited above, will naturally elect to control the flow rates in the 4 zones in a manner which corresponds exactly to the synchronous flow rate (100% of the synchronous flow rate).

One example of a SMB separation device of great industrial importance concerns the separation of aromatic C8 cuts with a view to producing para-xylene of commercial purity, typically at least 99.7% by weight, and a raffinate rich in ethylbenzene, ortho-xylene and meta-xylene.

The two preceding cited implementations can achieve the aim of commercial purity. However, the Applicant has demonstrated that while the teaching of the "synchronous flushes" of U.S. Pat. Nos. 5,972,224 and 6,110,364 constitutes a distinct improvement over the prior art, it is surprisingly possible to further improve the operation and performance of the simulated moving bed separation process by refining the rules defining the various flow rates of the bypass lines.

Finally, application Ser. No. 08/04637 describes a bypass line device, the lines connecting all of the plates $P_i$, $P_{i+1}$ without distinguishing the parity of the index i, with a rule concerning the flow rates to be applied to each line, which rule is different depending on whether there is at least one closed bypass line on the zone under consideration or all of the bypass lines are open.

The present invention may be viewed as constituting an improvement to the application cited above insofar as the flow rate rules to be applied to each bypass line are defined for each of the various operational zones of the column.

Further, the present invention concerns a particular configuration of the bypass lines which connect two successive plates, the first plate having an even index or (in an exclusive manner) having an odd index, as described in patents FR-2 904 776 and FR-2 913 345.

BRIEF DESCRIPTION OF THE FIGURES

Zone 1 is represented by the curve with diamonds.
Zone 2 is represented by the curve with squares.
Zone 3 is represented by the curve with triangles.
Zone 4 is represented by the curve with circles.

SIMPLIFIED DESCRIPTION OF THE INVENTION

The invention concerns an improved simulated moving bed separation device termed a SMB device.

More precisely, the invention is in the context of SMB units with a single chamber for distribution or extraction of the various fluids, each plate being divided into a certain number of panels and each panel being provided with a chamber for fluid distribution and extraction.

Further, the SMB units concerned by the present invention are units in which the bypass lines connect two consecutive plates, i.e. $P_i$ and $P_{i+1}$, but the index i is either even throughout the column or (in a manner which is exclusive from the foregoing) odd throughout the column.

It has surprisingly been discovered that the ideal operation of the bypass lines does not correspond to a strictly synchronous flow over the entirety of the SMB operational zones, but at a differentiated rate which is a function of the SMB zones and which can in some cases present an oversynchronicity of a greater or lesser degree.

More precisely, the present invention can be defined as a process for simulated moving bed (SMB) separation of a feed F in a SMB device having at least one column, said column being composed of a plurality of beds of adsorbants separated by plates $P_i$ each comprising at least one distribution/extraction system, in which process the feed F and a desorbent D are supplied, and at least one extract E and at least one raffinate R are withdrawn, the supply and withdrawal points being shifted over time by a value corresponding to one bed of adsorbant with a switch time ST, and determining a plurality of operational zones of the SMB, and in particular the following 4 principal zones:
  a zone 1 for desorption of the compounds produced in the extract, included between the supply of the desorbent D and the withdrawal of the extract E;
  a zone 2 for desorption of the compounds produced in the raffinate R, included between the withdrawal of the extract E and the supply of the feed F;
  a zone 3 for adsorption of compounds produced in the extract E, included between the supply of the feed F and the withdrawal of the raffinate R;
  a zone 4 located between the withdrawal of the raffinate R and the supply of the desorbent D;
the device further comprising external bypass lines $L_{i/i+1}$ directly joining two successive plates $P_i$, $P_{i+1}$, the index i being either even throughout the column or (in a manner which is exclusive from the foregoing) odd throughout the column, and allowing said plates to be flushed, in which device each of the bypass lines $L_{i/i+1}$ includes automated means for regulating the flow rate in the bypass line, the degree of opening of said regulating means being defined by the following three rules:
a) establishing a flow rate corresponding to an oversynchronicity in the range 15% to 30% in all of the open bypass lines of zone 1;
b) establishing a flow rate corresponding to the synchronicity within plus or minus 8% in all of the open bypass lines of zones 2 and 3;
c) establishing a flow rate corresponding to an oversynchronicity in the range 20% to 40% in all of the open bypass lines of zone 4.

The synchronicity flow rate is defined by $(V_i + V_{i+1} + VL_{i/i+1})/ST$, in which expression:
  $V_i$ denotes the volume of the distribution/extraction system of the outflow plate $P_i$;
  $V_{i+1}$ denotes the volume of the distribution/extraction system of the inflow plate $P_{i+1}$;
  $VL_{i/i+1}$ denotes the volume of the bypass line between $P_i$ and $P_{i+1}$;
  And ST denotes the switch time.

The oversynchronicity is defined by the formula:

Oversynchronicity=(actual flow rate in bypass line under consideration/synchronicity flow rate)−1.

In a particular case of the process of the invention, all of the open bypass lines belonging to the same zone have the same degree of synchronicity within plus or minus 2%.

The present invention also concerns a method for regulating the flow rates in the bypass lines of a simulated moving bed process comprising at least 4 operational zones defined by:
  a zone 1 for desorption of the compounds produced in the extract, included between the supply of the desorbent D and the withdrawal of the extract E;
  a zone 2 for desorption of the compounds produced in the raffinate, included between the withdrawal of the extract E and the supply of the feed F;
  a zone 3 for adsorption of compounds produced in the extract, included between the supply of the feed F and the withdrawal of the raffinate R;
  a zone 4 located between the withdrawal of the raffinate R and the supply of the desorbent D;
in which method:
  1) the optimum synchronicity over a given zone is determined by fixing the synchronicity at 100% for all of the unclosed bypass lines of the other zones;
  2) and the optimum synchronicity obtained in the preceding step is attributed to each zone.

In particular, the present invention is applicable to a simulated moving bed separation process for separating para-xylene from a mixture of aromatic C8 hydrocarbons.

In particular, the present invention can be applied to a simulated moving bed separation process for separating meta-xylene from a mixture of aromatic C8 hydrocarbons.

DETAILED DESCRIPTION OF THE INVENTION

The invention concerns an improved device for simulated moving bed separation known as a SMB device.

More precisely, the invention comes into the category of SMB units with a single chamber for distribution or extraction of various fluids, each plate being divided into a certain number of panels, and each panel being equipped with one chamber for the distribution and extraction of fluids.

Further, the SMB units concerned by the present invention are units in which the bypass lines connect two consecutive plates, i.e. $P_i$ and $P_{i+1}$, but the index i is either even or (exclusively from the foregoing) odd, this being throughout the column.

As an example, one configuration for the bypass line lines connects plates 1,2 then 3,4 then 5,6 and so on up to the last plate of the column which should preferably have an even index.

Another configuration for the bypass lines connects plates 2,3 then 4,5 then 6,7 and so on up to the last plate of the column which should preferably have an odd index.

It has surprisingly been discovered that the ideal operation of the bypass lines does not correspond to a strictly synchronous flow over all of the operational zones of the SMB, but to a differentiated flow rate depending on the zones of the SMB which can in some cases have a more or less marked oversynchronicity.

The term "oversynchronicity" means a value exceeding the value corresponding to synchronicity by at least 8%, and which can be expressed as a percentage above said synchronicity.

More precisely, the present invention defines over certain zones of the SMB unit a range of bypass line flow rates including a certain degree of specific oversynchronicity at the zone under consideration.

This results in a complex optimum in the set of bypass line flow rates, which depends on the zone of the SMB under consideration. This technical problem is completely absent from the teaching of the prior art and constitutes an increase in knowledge and expertise in SMB type processes.

Thus, the present invention concerns a process for simulated moving bed (SMB) separation of a feed F in a SMB device having at least one column, said column being composed of a plurality of beds of adsorbants separated by plates $P_i$ each comprising at least one distribution/extraction system, in which process the feed F and a desorbent D are supplied, and at least one extract E and at least one raffinate R are withdrawn, the supply and withdrawal points being shifted over time by a value corresponding to one bed of adsorbant with a switch time ST, and determining a plurality of operational zones of the SMB, and in particular the following 4 principal zones:

- a zone 1 for desorption of the compounds produced in the extract, included between the supply of the desorbent D and the withdrawal of the extract E;
- a zone 2 for desorption of the compounds produced in the raffinate, included between the withdrawal of the extract E and the supply of the feed F;
- a zone 3 for adsorption of compounds produced in the extract E, included between the supply of the feed F and the withdrawal of the raffinate R;
- a zone 4 located between the withdrawal of the raffinate R and the supply of the desorbent D;

the device further comprising external bypass lines $L_{i/i+1}$ directly joining two successive plates $P_i$, $P_{i+1}$, the index i being either even throughout the column or (in an exclusive manner) odd throughout the column, and allowing said plates to be flushed, in which each of the bypass lines $L_{i/i+1}$ includes automated means for regulating the flush flow rate, the degree of opening of said regulating means being defined by the following three rules:

a) establishing a flow rate corresponding to an oversynchronicity in the range 15% to 30% in all of the open bypass lines of zone 1;
b) establishing a flow rate corresponding to the synchronicity within plus or minus 8% in all of the open bypass lines of zones 2 and 3;
c) establishing a flow rate corresponding to an oversynchronicity in the range 20% to 40% in all of the open bypass lines of zone 4.

The synchronicity flow rate is defined by $(V_i+V_{i+1}+VL_{i/i+1})/ST$, in which expression:
- $V_i$ denotes the volume of the distribution/extraction system of the outflow plate $P_i$;
- $V_{i+1}$ denotes the volume of the distribution/extraction system of the inflow plate $P_{i+1}$;
- $VL_{i/i+1}$ denotes the volume of the bypass line between $P_i$ and $P_{i+1}$;
- and ST denotes the switch time.

The oversynchronicity is defined by the formula:

Oversynchronicity=(actual flow rate in bypass line under consideration/synchronicity flow rate)−1.

In a particular case of the simulated moving bed (SMB) separation process of the invention, all of the open bypass lines belonging to the same zone have the same degree of synchronicity within plus or minus 2%.

In the process of the invention, then, a bed i framed by a bypass line joining the upstream plate with index i and the downstream plate with index i+1 alternates with a bed i+1 which is not framed by any bypass line. It has been observed that it is particularly advantageous to differentiate the volumes of these two types of beds, i.e. the beds framed by a bypass line are denoted as a bed of type B and beds not framed by a bypass line are denoted as a bed of type A.

The beds of type A preferably have a volume ($V_A$) which is greater than or equal to that of the beds of type B ($V_B$) such that the transit time for the concentration profiles is the same in both types of bed.

Let $Qv_A$ and $Qv_B$ respectively be the mean volume flow rates during a cycle in bed A and in bed B.

The mean flow rate during a cycle in a bed denoted J can be calculated as follows:

$$Qv_J = \frac{\sum_{i=1}^{N_{step}} Qv_J^{stepi}}{N_{step}}$$

where $Qv_J^{stepi}$ is the volume flow rate in bed J during step i, and where $N_{step}$ is the number of steps of the cycle.

Similarly, the mean flow rate in a bypass line can be calculated as follows:

$$Q_{LDJ} = \frac{\sum_{i=1}^{N_{step}} Q_{LDJ}^{stepi}}{N_{step}}$$

where $Q_{LDJ}^{stepi}$ is the volume flow rate in the bypass line $L_{J/J+1}$ during step i;

$Q_{LDJ}^{stepi}$ is zero when the bypass line $L_{J/J+1}$ is closed.

In the case in which the adsorbant is identical in beds A and B, we thus have $$Qv_A = Qv_B + Q_{LDB}$$

The volume $V_A$ will then preferably be determined by the following inequalities:

$$V_B \leq V_A \leq V_B\left(1 + \frac{Q_{LDB}}{Qv_B}\right)$$

It is also possible to compensate for the absence of a bypass line framing bed A by causing the porosity between beds A and B to be varied (for example by causing the volume of the free space between the surface of the adsorbant bed and the upstream plate to be varied). The porosity $\epsilon_A$ will then preferably be determined by the following inequalities:

$$\varepsilon_B \leq \varepsilon_A \leq \varepsilon_B\left(1 + \frac{V_{LD}}{V_{bed}}\right)$$

It is also possible to compensate for the absence of a bypass line framing bed A by selecting a different adsorbant for beds with type A and type B (difference in porosity or adsorption capacity of adsorbant).

A combination of these different compensation modes is also possible.

The present invention also concerns a method for adjusting the flow rates in the bypass lines for each operational zone constituting the SMB column which may be defined in the following manner:
1) determining the optimum synchronicity for a given zone by fixing the synchronicity at 100% for all of the unclosed bypass lines of the other zones;
2) attributing to each zone the optimum synchronicity obtained in the preceding step.

Finally, the process of the present invention or the method of the invention is more particularly applicable to the separation of para-xylene or meta-xylene in a mixture of aromatic C8 hydrocarbons.

These two examples of applications are in no way limiting and other applications are possible, in particular in the field of separating normal and iso-paraffins or normal and iso-olefins.

EXAMPLES

The invention will be better understood from the following examples.

Example 1

A SMB unit was considered which was constituted by 24 beds, with a length of 1.1 m and an internal radius of 3.5 m, with a feed injection, a desorbent injection (could also be termed the eluent or solvent), an extract withdrawal and a raffinate withdrawal. The plates were single-chambered.

The total volume ($V_i + V_{i+1} + VL_{i/i+1}$) where $VL_{i/i+1}$ is the volume of the bypass line of plate $P_i$ at plate $P_{i+1}$ and in which $V_i$ is the volume of the distribution/extraction system of plate $P_i$, represented 3% of the volume of the bed included between the plate $P_i$ and the plate $P_{i+1}$.

The bypass lines connected the even plates to the odd plates (and thus connected the plates located upstream and downstream of even numbered beds of absorbent).

The beds were distributed in the configuration 5/9/7/3, i.e. the distribution of the beds was as follows:
5 beds in zone 1;
9 beds in zone 2;
7 beds in zone 3;
3 beds in zone 4.

The adsorbant used was a zeolite of type BaX, and the eluent was para-diethylbenzene.

The temperature was 175° C. and the pressure was 15 bar (1 bar=$10^5$ Pascal).

The feed was composed of 20% para-xylene, 24% ortho xylene, 51% of meta-xylene and 5% of ethylbenzene. The switch time used was 70.8 seconds.

The liquid flow rates for injection of the feed and desorbent were as follows:
6.81 m$^3$·min$^{-1}$ for the feed;
7.48 m$^3$·min$^{-1}$ for the desorbent.
i.e. a solvent ratio SIF=1.1.

When the synchronicity was adjusted to 100% for all of the open bypass lines, a para-xylene purity of 99.76% and a para-xylene yield of 95.80% were obtained by simulation.

The variation in the performances of the SMB, measured in terms of PX yield at a fixed desorbent flow rate, feed flow rate, purity of produced para-xylene and switch time, as a function of the synchronicity of all of the unclosed bypass lines of a zone, was calculated for each of the zones, retaining a synchronicity of 100% for all of the unclosed bypass lines of the other zones.

Figure 1:
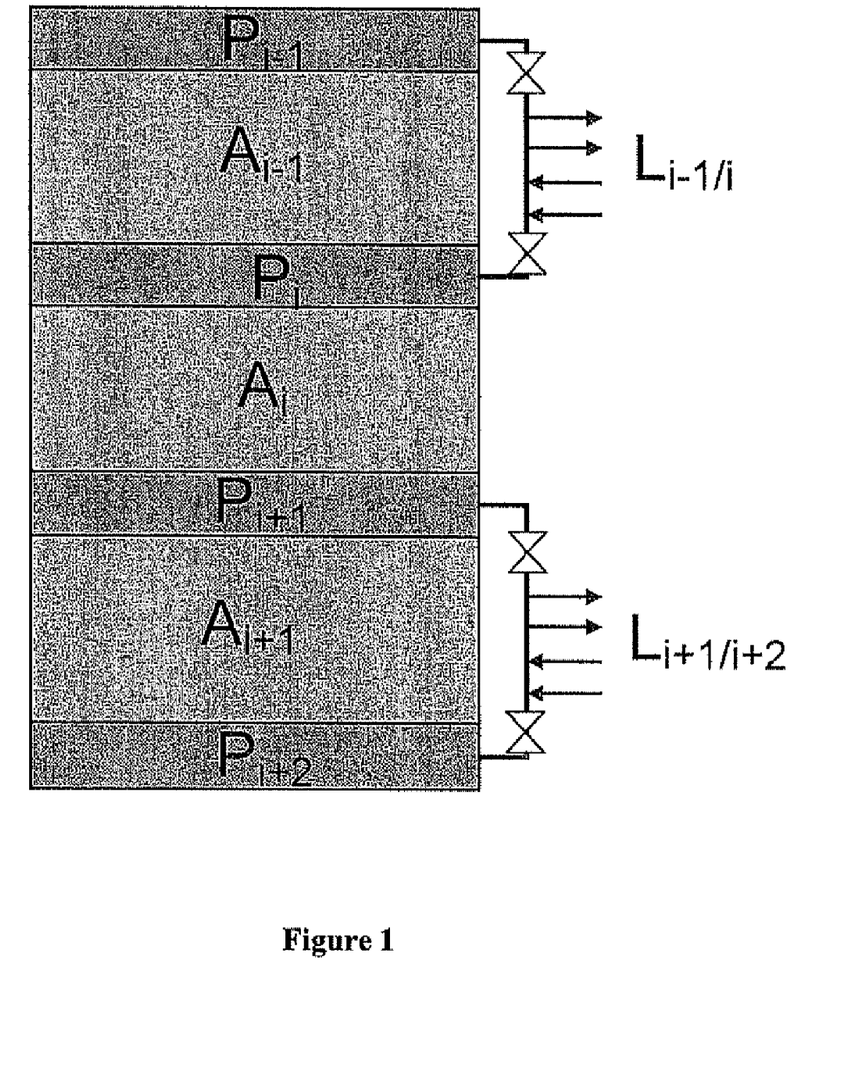
FIG. 1 represents a succession of 4 beds $P_{i-1}$, $P_i$, $P_{i+1}$, $P_{1+2}$ forming part of a simulated moving bed (SMB) column. The bypass line lines $L_{i-i/i}$ and $L_{i+1/i+2}$ are located between the plates $P_{i-1}$ and $P_i$ and between plates $P_{i+1}$ and $P_{i+2}$.
Figure 2:
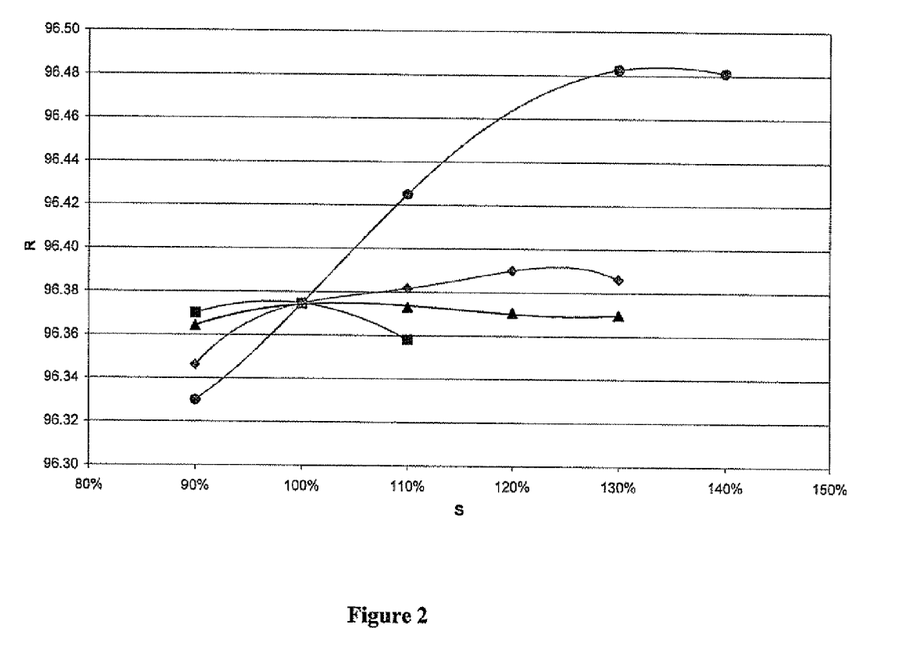
FIG. 2 shows the variations in the performance of the SMB measured in terms of PX yield at a fixed desorbent flow rate, feed flow rate, purity of the para-xylene produced and switch time, as a function of the synchronicity of all of the unclosed bypass lines for each of the zones, conserving a synchronicity of 100% for all of the unclosed bypass lines of the other zones.

This variation in the performances of the SMB is illustrated in FIG. 2 for each of the various zones. The PX yield is the ratio between the quantity of PX withdrawn in the extract and the quantity of PX injected.

Zone 1 is represented by the curve with diamonds.
Zone 2 is represented by the curve with squares.
Zone 3 is represented by the curve with triangles.
Zone 4 is represented by the curve with circles.

The yields at the optimum synchronicity obtained for each zone at iso-purity, feed flow rate, switch time and solvent ratio are given in the table below.

|        | Optimum synchronicity | Yield  |
|--------|----------------------|--------|
| Zone 1 | 120%                 | 96.39% |
| Zone 2 | 100%                 | 96.37% |
| Zone 3 | 100%                 | 96.37% |
| Zone 4 | 130%                 | 96.48% |

After determining the optimum zone by zone, the four optimized values for synchronicity, i.e. 120% in zone 1, 100% in zone 2, 100% in zone 3 and 130% in zone 4, were imposed simultaneously.

At iso-purity, feed flow rate, switch time and solvent ratio, a yield of 96.50% was obtained, which was greater than the yields obtained when the synchronicity was adjusted in one zone only.

It is clear that using a synchronicity which is differentiated according to the zones results in a substantially improved yield compared with the case of 100% synchronicity for all of the open bypass lines.

Example 2

A SMB unit was considered which was constituted by 24 beds, with an internal radius of 3.5 m, with a feed injection, a desorbent injection (could also be termed the eluent or solvent), an extract withdrawal and a raffinate withdrawal. The plates were single-chambered.

The total volume ($V_i + V_{i+1} + VL_{i/i+1}$) where $VL_{i/i+1}$ is the volume of the bypass line of the plate $P_i$ at plate $P_{i+1}$ and in which $V_i$ is the volume of the distribution/extraction system of plate $P_i$, represented 3% of the volume of the bed included between the plate $P_i$ and the plate $P_{i+1}$.

The bypass lines connected the even plates to odd plates (and thus connected the plates located upstream and downstream of even numbered beds of absorbent).

The even beds were 1.08 m long while the odd beds were 1.11 m long, in order to compensate for the differences in flow rate between the short-circuited beds and the beds which were not short-circuited.

The beds were distributed in the configuration 5/9/7/3, i.e. the distribution of the beds was as follows:
5 beds in zone 1;
9 beds in zone 2;
7 beds in zone 3;
3 beds in zone 4.

The adsorbant used was a zeolite of type BaX, and the eluent was para-diethylbenzene.

The temperature was 175° C. and the pressure was 15 bar (1 bar=$10^5$ Pascal).

The feed was composed of 20% para-xylene, 24% ortho xylene, 51% of meta xylene and 5% of ethylbenzene. The switch time used was 70.8 seconds.

The liquid flow rates for injection of the feed and desorbent were as follows:
6.81 m$^3$·min$^{-1}$ for the feed;
7.48 m$^3$·min$^{-1}$ for the desorbent.
i.e. a solvent ratio S/F=1.1.

When the synchronicity was adjusted to 100% for all of the open bypass lines, a para-xylene purity of 99.76% and a para-xylene yield of 95.98% were obtained by simulation.

The variation in the performances of the SMB, measured in terms of PX yield at a fixed desorbent flow rate, feed flow rate, purity of produced para-xylene and switch time, as a function of the synchronicity of all of the unclosed bypass lines of a zone, was calculated for each of the zones, retaining a synchronicity of 100% for all of the unclosed bypass lines of the other zones.

This variation in the performances of the SMB is illustrated in FIG. 2 for each of the various zones. The PX yield is the ratio between the quantity of PX withdrawn in the extract and the quantity of PX injected.

Zone 1 is represented by the curve with diamonds.
Zone 2 is represented by the curve with squares.
Zone 3 is represented by the curve with triangles.
Zone 4 is represented by the curve with circles.

The yields at the optimum synchronicity obtained for each zone at 99.76% iso-purity, feed flow rate, switch time and solvent ratio are given in the table below.

|        | Optimum synchronicity | Yield   |
| ------ | --------------------- | ------- |
| Zone 1 | 120%                  | 96.56%  |
| Zone 2 | 100%                  | 96.53%  |
| Zone 3 | 100%                  | 96.53%  |
| Zone 4 | 130%                  | 96.67%  |

After determining the optimum zone by zone, the four optimized values for synchronicity, i.e. 120% in zone 1, 100% in zone 2, 100% in zone 3 and 130% in zone 4, were imposed simultaneously.

At iso-purity, feed flow rate, switch time and solvent ratio, a yield of 96.70% was obtained, which was greater than the yields obtained when the synchronicity was adjusted in one zone only.

It is clear that using a synchronicity which is differentiated according to zones as well as compensating for the volume of the bypass lines results in an even more improved yield compared with using differentiated synchronicity with no volume compensation.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosures of all applications, patents and publications, cited herein and of corresponding French application No. 09/01784, filed Apr. 10, 2009, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for simulated moving bed (SMB) separation of a feed F in a SMB device having at least one column, said column being composed of a plurality of beds of adsorbants separated by plates $P_i$ each comprising at least one distribution/extraction system, in which process the feed F and a desorbent D are supplied, and at least one extract E and at least one raffinate R are withdrawn, the supply and withdrawal points being shifted over time by a value corresponding to one bed of adsorbant with a switch time ST, and determining a plurality of operational zones of the SMB, and in particular the following 4 principal zones:

a zone 1 for desorption of the compounds produced in the extract, included between the supply of the desorbent D and the withdrawal of the extract E;

a zone 2 for desorption of the compounds produced in the raffinate, included between the withdrawal of the extract E and the supply of the feed F;

a zone 3 for adsorption of compounds produced in the extract, included between the supply of the feed and the withdrawal of the raffinate R;

a zone 4 located between the withdrawal of the raffinate R and the supply of the desorbent D;

the device further comprising external bypass lines $L_{i/i+1}$ directly joining two successive plates $P_i$, $P_{i+1}$, the index i being either even throughout the column or, in a manner which is exclusive from the foregoing, odd throughout the column, and allowing said plates to be flushed, in which device each of the bypass lines $L_{i/i+1}$ includes automated means for regulating the flow rate in the bypass line, the degree of opening of said regulating means being defined by the following three rules:

a) establishing a flow rate corresponding to an oversynchronicity in the range 15% to 30% in all of the open bypass lines of zone 1;

b) establishing a flow rate corresponding to the synchronicity within plus or minus 8% in all of the open bypass lines of zones 2 and 3;

c) establishing a flow rate corresponding to an oversynchronicity in the range 20% to 40% in all of the open bypass lines of zone 4;

the synchronicity flow rate being defined by $(V_i + V_{i+1} + VL_{i,i+1})/ST$, in which expression:

$V_i$ denotes the volume of the distribution/extraction system of the outflow plate $P_i$;

$V_{i+1}$ denotes the volume of the distribution/extraction system of the inflow plate $P_{i+1}$;

$VL_{i/i+1}$ denotes the volume of the bypass line between $P_i$ and $P_{i+1}$; and ST denotes the switch time;

the oversynchronicity being defined by the formula:

oversynchronicity=(actual flow rate in bypass line under consideration/synchronicity flow rate)−1.

2. A simulated moving bed separation process according to claim 1, in which all of the open bypass lines belonging to the same zone have the same degree of synchronicity within plus or minus 2%.

3. A simulated moving bed separation process according to claim 1, in which the beds not having bypass lines joining the downstream plate and the upstream plate of said bed, termed type A beds, have a volume ($V_A$) which is greater than or equal to the volume ($V_B$) of the beds having bypass lines, termed type B beds, in accordance with the relationships:

$$V_B \leq V_A \leq V_B\left(1 + \frac{Q_{LDB}}{Qv_B}\right)$$

where $Qv_B$ is the mean volume flow rate during a cycle in bed B and $Q_{LDB}$ is the mean volume flow rate during a cycle in the bypass line framing a bed of type B.

4. A simulated moving bed separation process according to claim 1, in which the beds not having bypass lines joining the downstream plate and the upstream plate of said bed, termed type A beds, have a porosity ($\epsilon_A$) which is greater than or equal to the porosity ($\epsilon_B$) of the bed having bypass lines, termed beds of type B, in accordance with the relationships:

$$\epsilon_B \leq \epsilon_A \leq \epsilon_B\left(1 + \frac{V_{LD}}{V_{bed}}\right)$$

where $V_{LD}$ is the volume of the bypass line framing a bed of type B and $V_{bed}$ is the volume of one bed.

5. A simulated moving bed separation process according to claim 1, in which the beds not having bypass lines joining the downstream plate and the upstream plate of said bed, termed a bed of type A, are filled with an adsorbant having an intragranular porosity and/or an adsorption capacity which is greater than that of the beds having bypass lines, termed a bed of type B, such that the transit time of said concentration profiles is the same in both types of beds.

6. A method for regulating the flow rates in the bypass lines per operational zone in a simulated moving bed process according to claim 1 comprising at least 4 operational zones defined by:

a zone 1 for desorption of the compounds produced in the extract, included between the supply of the desorbent D and the withdrawal of the extract E;

a zone 2 for desorption of the compounds produced in the raffinate, included between the withdrawal of the extract E and the supply of the feed F;

a zone 3 for adsorption of compounds produced in the extract, included between the supply of the feed F and the withdrawal of the raffinate R;

a zone 4 located between the withdrawal of the raffinate R and the supply of the desorbent D;

in which method:
1) the optimum synchronicity over a given zone is determined by fixing the synchronicity at 100% for all of the unclosed bypass lines of the other zones;
2) and the optimum synchronicity obtained in the preceding step is attributed to each zone.

7. Use of a simulated moving bed separation process according to claim 1, for the separation of para-xylene or meta-xylene in a mixture of aromatic C8 hydrocarbons.

* * * * *